United States Patent [19]

Blangetti et al.

[11] Patent Number: 4,729,667

[45] Date of Patent: Mar. 8, 1988

[54] PROCESS AND DEVICE FOR THE DETERMINATION OF THE THERMAL RESISTANCE OF CONTAMINATED HEAT EXCHANGE ELEMENTS OF THERMODYNAMIC APPARATUSES, IN PARTICULAR OF POWER STATION CONDENSERS

[75] Inventors: Francisco Blangetti, Wettingen; Reinhard Müller, Baden, both of Switzerland; Helmut Lang, Plainsboro, N.J.

[73] Assignee: BBC Brown, Boveri & Company, Limited, Baden, Switzerland

[21] Appl. No.: 874,644

[22] Filed: Jun. 16, 1986

[30] Foreign Application Priority Data

Jun. 17, 1985 [CH] Switzerland .................. 2553/85

[51] Int. Cl.⁴ .................. G01N 25/20; G01N 25/00
[52] U.S. Cl. .......................... 374/43; 374/7; 165/11.1
[58] Field of Search .............. 374/7, 43, 45, 57; 73/61.2, 61.3; 165/11.1

[56] References Cited

U.S. PATENT DOCUMENTS

| | | | |
|---|---|---|---|
| 3,312,274 | 4/1967 | Sebald | 165/11.1 |
| 3,913,378 | 10/1975 | Hausler | 374/7 |
| 3,918,300 | 11/1975 | Weisstuch et al. | 374/7 |
| 4,024,751 | 5/1977 | Potzrebowski | 374/43 |
| 4,044,605 | 8/1977 | Bratthall | 73/61.2 |
| 4,138,878 | 2/1979 | Holmes et al. | 374/7 |
| 4,383,438 | 5/1983 | Eaton | 374/7 |
| 4,396,300 | 8/1983 | Characklis et al. | 374/43 |
| 4,466,277 | 8/1984 | Baier et al. | 73/61.2 |
| 4,479,727 | 10/1984 | Domingorena et al. | 374/43 |

FOREIGN PATENT DOCUMENTS

| | | | |
|---|---|---|---|
| 1937965 | 4/1970 | Fed. Rep. of Germany | 165/11.1 |
| 0777386 | 11/1980 | U.S.S.R. | 165/11.1 |

*Primary Examiner*—Charles Frankfort
*Assistant Examiner*—Thomas B. Will
*Attorney, Agent, or Firm*—Burns, Doane, Swecker & Mathis

[57] ABSTRACT

The process consists in that two comparison tube sections (3; 4), which originate from a single condenser tube and of which one (3) is left in the corroded condition and/or the condition encrusted by mineral deposits and the other (4) is brought into the new condition by etching or other cleaning procedures, are conductively connected in series, and cooling water flows through them and they are heated from the outside in a condenser chamber in each case (1 and 2 respectively) by steam flows of equal power. The temperatures ($t_1$, $t_2$ and $t_3$, $t_4$ respectively) measured at the inlet and outlet positions of the comparison tube sections (3; 4), the measured values of the mass flow of cooling water ($M_w$) and the steam temperatures ($t_f$, $t_b$) and the heat flows ($Q_{kf}=Q_{kb}$) in the two condenser chambers (1 and 2 respectively) permit the determination of the thermal resistance ($R_f$) of the incrustation layer of the tube drawn for the purposes of investigation from the condenser. A device for carrying out the process exhibits two condenser chambers (1; 2) to receive the comparison tube sections (3; 4) and a degassing vessel 11, which communicates with the condenser chambers (1; 2). In a cooling water duct (15+5+16) there are provided, before and after the condenser chambers (1; 2), measurement chambers (17 and 19, 18 respectively) with thermo-elements for the measurement of the differences of the said cooling water and steam temperatures. Precision wattmeters preferably serve for the measurement of the heat flows ($Q_{kf}=Q_{kb}$). The heat flows can also be calculated from the difference in enthalpy of the mass flow of the cooling water ($M_w$) before and after the condenser chambers (1; 2). The measurement of the mass flow of cooling water ($M_w$) preferably takes place by weighing the quantity of cooling water which has flowed out in unit time.

4 Claims, 3 Drawing Figures

PROCESS AND DEVICE FOR THE DETERMINATION OF THE THERMAL RESISTANCE OF CONTAMINATED HEAT EXCHANGE ELEMENTS OF THERMODYNAMIC APPARATUSES, IN PARTICULAR OF POWER STATION CONDENSERS

FIELD OF THE INVENTION

The present invention relates to a process and a device for the determination of the thermal resistance of contaminated heat exchange elements of thermodynamic apparatuses in general and, in particular, of power station condensers.

BACKGROUND OF THE INVENTION

In thermodynamic apparatuses, and in particular in power station condensers, for which the present invention is principally devised, the coefficient of thermal transmission or the reciprocal thereof, i.e. the thermal resistance, is in certain circumstances substantially impaired at the heat exchanger surfaces after a greater or lesser length of operating time by the formation of corrosion products and/or mineral and organic deposits from the cooling water.

This can be counteracted by a continuously operating cleaning system and the addition of corrosion-inhibiting additives to the cooling water, as a result of which a thin, lasting and properly adhering protective layer is formed at the heat exchanger surfaces. Since this layer does of course likewise impair the heat transmission, it is referred to as a protective/dirt layer.

In order to determine whether the overall coefficient of heat transmission still complies with the guaranteed values indicated by the manufacturer, it must be possible for the thermal resistance of this protective/dirt layer to be determined by the customer in the event of a decrease therein after a certain period of operation. A process for the experimental determination of this thermal resistance is described in the ASME publication PTC 12.2, section 5. However, this widespread process is costly, involves a relatively lengthy interruption in operation and is of low accuracy. Accordingly, in the circumstances in which importance is placed on greater accuracy, there is reluctance to carry out the measurement in accordance with this method, since it does not permit a reliable determination of the effect of the factors which are of decisive importance to the coefficient of heat transmission. In this connection, however, the thermal resistance of the protective/dirt layer is only an experimentally unconfirmed assumption, by means of which the difference between the previously calculated and the experimentally determined thermal resistance is to be explained. With such an acceptance test, it is not possible to obtain indications regarding optimization of the elements and other design data of the condenser, such as piping, steam flowrate, cooling water flowrate etc.

The principle of this process according to ASME consists essentially of the following: after shutdown and cooling of the condenser, from each respective set of 2,000 tubes of a bundle of tubes a set of for example seven tubes is selected, consisting of a central tube and six outer tubes, which surround the central tube in the form of a hexagon. The central one of these tubes is replaced by a new one, which has the same new condition as was exhibited by the remaining tubes of the bundle of tubes when the tubes were fitted to the condenser. In order to withdraw the replaced central tube and to introduce the new tube, manhole covers are provided in the two water chambers at the pertinent positions. The seven tubes selected for examination, i.e. the central new tube and the six old tubes surrounding the latter, are connected at their two ends to hoses, which are guided outwardly through the water chambers and the said manholes and are connected to an external cooling water stream. All seven tubes carry cooling water under the same conditions, and steam of the same condition circulates around them. By means of measuring instruments for the mass flow of cooling water and for the inlet and outlet temperature of the cooling water at the inlet and outlet respectively of the cooling water from the selected seven tubes, the mean coefficient of heat transfer of the six outer tubes and the coefficient of heat transfer of the new tube are determined. The ratio of these two values is referred to as the purity factor. For this purity factor, a simple mathematical expression is obtained, which however exhibits the error that the unknown thermal conductivity coefficient of the layer deposited in the old tubes is not included therein. The process is accordingly indeed unreliable, but, as has been mentioned, has nevertheless found widespread application. However, in circumstances in which more accurate results are required, it is not sufficiently reliable, so that a requirement exists for a more accurate test method for the determination of the change in the coefficient of heat transmission of a condenser or similar apparatus having heat exchanger surfaces.

OBJECT AND SUMMARY OF THE INVENTION

It is an object of the present invention to provide an accurate test method for determining the change in the coefficient of heat transmission of a condenser or similar apparatus having heat exchanger surfaces. This object is met by a method and a device for performing the test method by means of which the initially mentioned disadvantages of the ASME method, in particular the inaccuracy thereof, are to be avoided.

BRIEF DESCRIPTION OF THE DRAWING

The invention is described in greater detail below, with reference to exemplary embodiments of the device according to the invention which are shown in the drawing.

In the drawing.

DETAILED DESCRIPTION OF A PREFERRED EMBODIMENT

Figure 1:
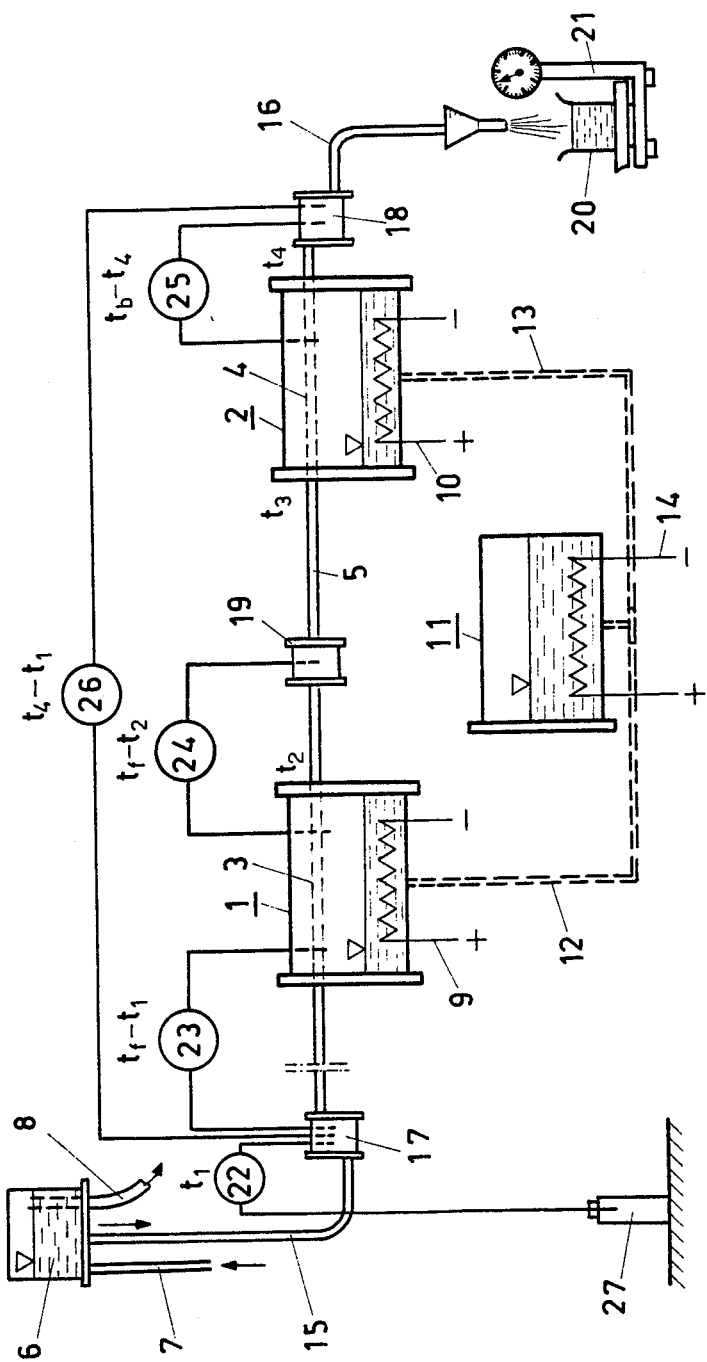
FIG. 1 is a schematic representation of a device according to the invention, with the principal components necessary in order to carry out the method.

The method, according to the invention, for the determination of the coefficient of heat transmission or of the thermal resistance of a contaminated tube is based on a comparison of the thermal resistances of two sections of the same tube, of which one section is left in the contaminated condition and the second is etched bright, in such a manner that the coating of corrosion, silt and the like is completely removed, while the tube material remains in its entirety. The two comparison tube sections 3 and 4 to be investigated are drawn into two horizontal condenser chambers 1 and 2 according to FIG. 1. In contrast to the ASME method, the comparison tube sections are obtained from only a single one of 2,000 tubes in each bundle of tubes, in that this tube selected for examination in one of the two water chambers is withdrawn in each instance by such a distance out of the tube plate as is permitted by the space in the water chamber, and the portion drawn out is separated at the tube plate. This takes place exclusively within the water chamber, since the latter usually has no manhole covers, through which the tube to be examined could be drawn into the open air. In the case of the conventional condenser sizes, there are obtained in this manner for example five comparison tube sections of length 1.20 to 1.80 m. The length of these tube sections 3 and 4 also determine the length of the condenser chambers 1 and 2, which are thermally insulated to the greatest possible extent. The tube sections 3 and 4 inserted into the chambers 1 and 2 are connected in series by a likewise thermally insulated connecting duct 5. Cooling water flows through the tube sections 3 and 4 from a reservoir 6, the water level of which and thus the static pressure level in relation to the height of the comparison tube sections are kept constant by the supply of water via a supply duct 7 and drawing-off of the excess water through an overflow duct 8.

The steam which flows around the tube sections 3 and 4 and condenses at the external surface thereof is generated by electrical heating elements 9, 10 at the base of the condenser chambers 1 and 2 respectively. The condensate dripping from the tube sections 3 and 4 is evaporated again at the base etc. In order to degas the water intended for evaporation in the two chambers 1 and 2, the fresh water, before it passes through the two hot water ducts 12 and 13 into the chambers 1 and 2 respectively, is boiled in a degassing vessel 11, and this likewise takes place by means of an electrical heating element 14.

The heating power in the three heating elements 9, 10 and 14 is measured by precision wattmeters and kept constant by regulators of known construction within a very narrow range.

The device according to FIG. 1 has crystallized out as the most suitable from a series of possible designs which were investigated, having one and two condenser chambers and various cooling water duct systems.

The contaminated comparison tube section 3 is clamped in the left-hand condenser chamber 1, and the bright-etched comparison tube section 4 in the right-hand condenser chamber 2, in which arrangement their ends are sealed by O-ring seals against the steam space of the condenser chambers in order to prevent the penetration of air.

The start of the tube section 3 is connected by a cooling water supply duct 15 to the reservoir 6, and the end of the tube section 4 is connected to a cooling water exhaust duct 16. Durring the test, being supplied from the reservoir 6, the two tube sections are flowed through through the supply duct 15 and via the connecting duct 5 in series. In order to be able to determine, in the manner described below, the change in the coefficient of heat transmission of the tube section which is contaminated as compared with the bright-etched tube section, there are provided in the set of cooling water ducts before the contaminated tube section and after the bright-etched tube section a forward, a rear and a central measurement chamber 17, 18 and 19 in each case, which provide the data required for the determination of the thermal resistance which is sought.

The cooling water entering the experimental apparatus is at room temperature, stands under constant pressure and its flowrate can be adjusted to the values occurring in the condensers by means of a valve, which is possibly integrated into the forward measurement chamber 17. The water temperatures $t_1$, $t_2$ and $t_4$ at the inlet to the contaminated tube section 3 and at its outlet respectively and at the outlet of the bright tube section 4 are measured by thermo-elements. Because of the good thermal insulation of the connecting duct 5, the temperature $t_3$ at the inlet of the bright tube section 4 can be assumed to be equal to $t_2$ at the outlet of the tube section 3. The mass flow of cooling water $\dot{M}_w$ is determined by weighing the weight of water which flows into a measurement vessel 20 on a dial balance 21 in a period of time determined by means of a stop-watch.

Distilled water is employed for the generation of the steam, and the evaporation takes place at a pressure below atmospheric pressure.

In order to determine the thermal resistance $R_f$ of the contaminated comparison tube section 3, in the manner indicated at the conclusion of the description, there is a requirement not only for quantities yet to be explained and the mentioned mass flow of cooling water $\dot{M}_w$, but also for the temperatures and temperatures differences evident from FIG. 1. The temperature difference indicators are shown by the reference numerals 22 to 26. They indicate the differences of the temperatures sensed by thermo-elements in the measurement chambers 17, 18 and 19. The reference temperature 0° C., proceeding from which the temperature $t_1$ is measured, prevails in a comparison measurement position 27, which is maintained at the freezing point of water by means of an ice/water mixture.

The degassing vessel 11 is at the same time a reservoir, from which the distilled water heated to boiling point passes into the condenser chambers 1 and 2, where it is evaporated by the heating elements 9 and 10 respectively. The heat flows supplied $Q_k$, which it is necessary to know in order to determine the thermal resistance $R_f$ of the contaminated tube section 3, can be and are determined, in order to improve the accuracy of measurement, both by the precision wattmeters connected in front of the heating elements and also by weighing of the quantity of cooling water which has flowed out in a measured period of time and division thereof by the flowing-out time as well as multiplication of the mass flow of cooling water $\dot{M}_w$, obtained in this manner, by the temperature difference $t_4 - t_1$ and the specific heat $c_{pw}$ at constant pressure for water.

The device shown in FIG. 1 exhibits the elements which are essentially sufficient to obtain the quantities required for the determination of $R_f$. However, in order to bring boiling water from the degassing vessel 11 into the condenser chambers 1 and 2, it would be necessary to generate a pressure in the vessel 11, e.g. by a pump (not shown).

Figure 2:
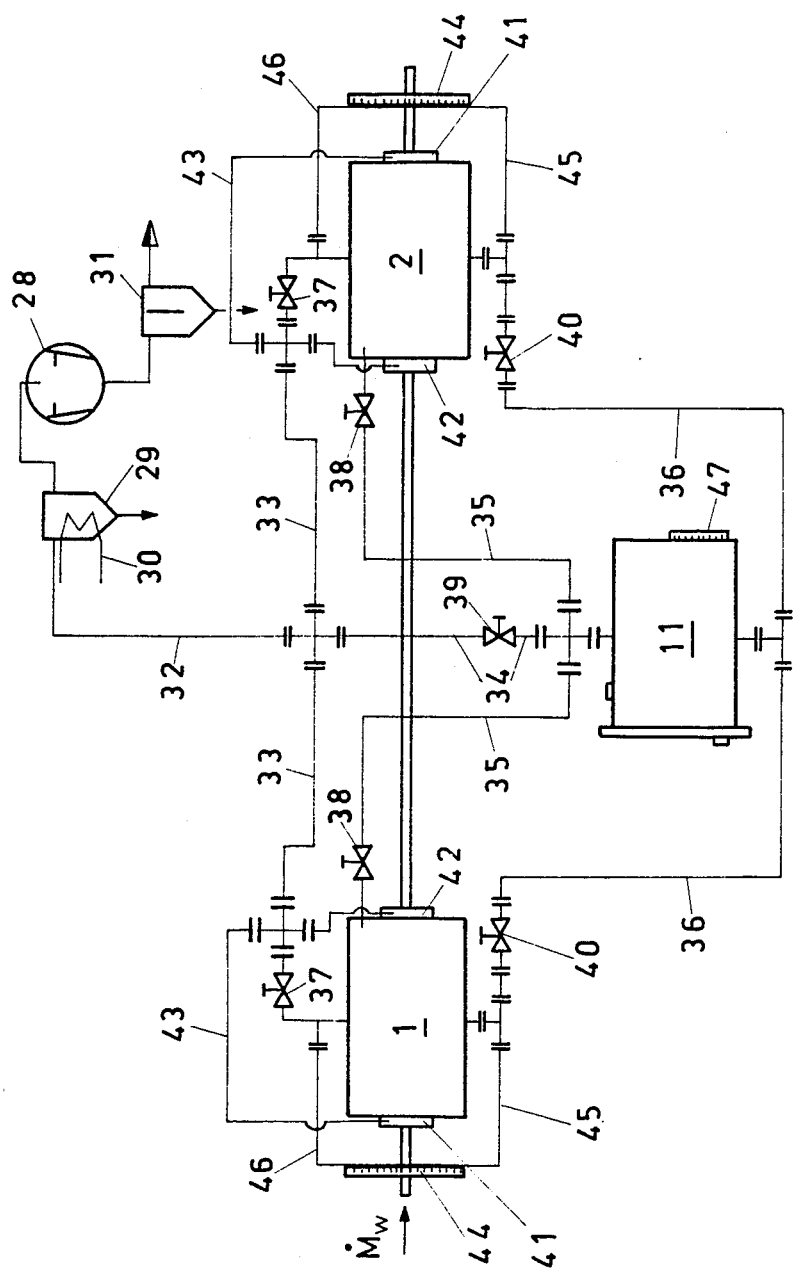
FIG. 2 is a schematic representation of an exhaust system for the production of a vacuum, as a further development of the system according to FIG. 1.

However, in the case of an embodiment according to FIG. 2, which is better equipped for the requirements in practice, having an evacuation device for the steam spaces of the chambers 1 and 2 and of the degassing vessel 11, such a pressure generator can be dispensed with.

For the sake of improved clarity, in FIG. 2 of the elements of the device represented in FIG. 1, besides the evacuation device, only the condenser chambers 1 and 2 and the degassing vessel 11 have been shown. The principal components of the evacuation device are a vacuum pump 28, a water separator 29 in front of the pump 28 with a cooling coil 30, a further water separator 31 after the pump 28, evacuation ducts 32, 33, 34, compensating ducts 35 and filling ducts 36. Valves 37 to 40 are provided in these ducts.

At the start of the test, with the vacuum pump 28 operating, the valve 39 is closed, and the valves 37 are open; the valves 40 are also open. Water is drawn into the chambers 1 and 2 from the degassing vessel 11 through the filling ducts 36 by means of the vaccum in the chambers 1 and 2. The compensating ducts ensure that the same pressure prevails in the two chambers. The water in the degassing vessel 11 and in the two chambers 1 and 2 is brought to boiling point by means of the electrical heating elements 14, and 9 and 10 respectively, in order to drive out the air content. A soon as a steady state has been achieved with cooling water flowing through, which state may be determined by constancy of the temperature differences to be read off at the temperature indicators 22 to 26, the valves 37, 38 and 39 are closed and the measurement procedure begins. During this, however, the vacuum pump continues in operation, in order to draw off any leakage steam possibly emerging at the sealing housings 41, 42 of the chambers 1 and 2 via leakage steam ducts 43. At the outer end surfaces of the chambers 1 and 2 there are provided water level indicators 44, which are connected via connecting ducts 45 and 46 to the water space or steam space of the condenser chambers 1 and 2. The degassing vessel 11 also has a water level indicator 47 at one end face.

With reference to the diagram shown in FIG. 3, which shows the temperature progression in the cooling water and in the steam space of the condenser chambers 1 and 2, there is shown below the path by means of which, with the physical quantities measured in the device, the desired difference between the thermal resistances of the contaminated and of the bright comparison tube sections 3 and 4 respectively can be determined. In this procedure, it is expedient to use, in place of the coefficients of heat transmission k, the reciprocal thereof $R = 1/k$, i.e. the thermal resistance.

The thermal resistance $R_f$ of the deposit in the contaminated tube is equal to the difference between the thermal resistance $1/k$ of the contaminated tube section 3 and the thermal resistance $1/k_b$ of the bright-etched tube section 4, expressed by the equation:

$$R_f = 1/k - 1/k_b.$$

On the assumption that the cooling water flowrate, the heat flows passing to the comparison tube sections 3 and 4 and the heat transfer surface areas = external surface areas of the tube sections in both condenser chambers 1 and 2 are equal, the following expressions can be established for the heat flows $\dot{Q}_k$ passing to the two comparison tube sections 3 and 4:

$$\dot{Q}_k = kA(t_2 - t_1)/\ln[(t_f - t_1)/(t_f - t_2)]$$

and $$\dot{Q}_k = k_b A(t_4 - t_3)/\ln[(t_b - t_3)/(t_b - t_4)],$$

wherein $t_2 = t_3$ is assumed and the subscripts f and b relate to the contaminated and bright-etched comparison tube sections respectively. The meanings of the remaining quantities, to the extent that these have not already been defined above, are as follows: A = heat transfer surface area = external surface area of the tube sections in m², $t_f$ = steam temperature in °C. in the condenser chamber 1 for the contaminated tube section 3, $t_b$ is the same for the bright tube section 4 in the condenser chamber 2, and ln signifies the natural logarithm.

On account of the equal steam-traversed lengths l and external diameters $d_a$ of the comparison tube sections 3, 4 and thus the equal condensation surface areas as well as the equal heat flows in the two condenser chambers 1 and 2, the following equation is obtained, provided that k and $k_b$ in the equation for $R_f$ are substituted by the expressions for k and $k_b$ obtained from the two equations for $\dot{Q}_k$:

$$R_f = \pi d_a L/\dot{Q}_k \cdot [(t_2 - t_1)/\ln\{(t_f - t_1)/(t_f - t_2)\} - (t_4 - t_2)/\ln\{(t_b - t_2)/(t_b - t_4)\}].$$

Accordingly, $R_f$ may readily be determined from the measured temperatures or temperature differences, the distance traversed by the steam and the external diameter of the two comparison tube sections and the heat flow supplied.

If it is assumed that the specific heat at constant pressure, cpw, of the cooling water is constant, then the expression for $R_f$ may be written in the following form, with $\dot{M}_w$, which, as described in the introduction, can be determined by weighing the quantity of water which has flowed out in a measured period of time:

$$R_f = \pi d_a L/\dot{M}_w c_{pw}[1/\ln\{(t_f - t_1)/(t_f - t_2)\} - 1/\ln\{(t_b - t_2)/(t_b - t_4)\}].$$

Accordingly, it is not necessary to measure $Q_k$, but the accurate measurement of $\dot{M}_w$ is sufficient, which can be carried out by simpler means.

The $R_f$ obtained in this manner for the comparison tube section 3 is now determined with the same bright-etched comparison tube section 4 in a similar manner for some of the remaining tube sections of the condenser tube which has been drawn, and the mean value is determined from the $R_f$ values obtained. As a rule, it is sufficient to investigate the first tube section 3 and three further contaminated tube sections.

For all further tubes drawn from 2,000 condenser tubes in each instance, the described procedure is repeated, and from the sum of the thus determined mean values there is formed, as the final result sought, a resulting mean value $R_{fres}$ of the condenser or of another thermodynamic apparatus with heat exchanger surfaces.

In contrast to the initially mentioned ASME method, the method according to the invention guarantees for the two tube sections 3 and 4 equal cooling water flowrates and virtually equal Reynolds numbers of the cooling water current as well as equal condensate loading in the two condenser chambers. The latter is particularly important, in order to obtain equal coefficients of heat transfer $\alpha_F$ for the condensate film on the external surface of the tube sections 3 and 4. According to Nusselt, the following proportionality is applicable to laminar condensate layers without shear stresses in the boundary layer: $\alpha_F M^{-\frac{1}{3}} Q^{-\frac{1}{3}}$, i.e. in other words, equal heat flows $Q_k$ also result in approximately equal values of $\alpha_F$. In order to obtain as far as possible equal temperatures in the two condenser chambers and to keep changes of the reference temperature for the calculation of the thermal properties of the condensate film as small as possible, the bright-etched tube section 4 is disposed, seen in the direction of the current passing through, after the contaminated tube section.

Figure 3:
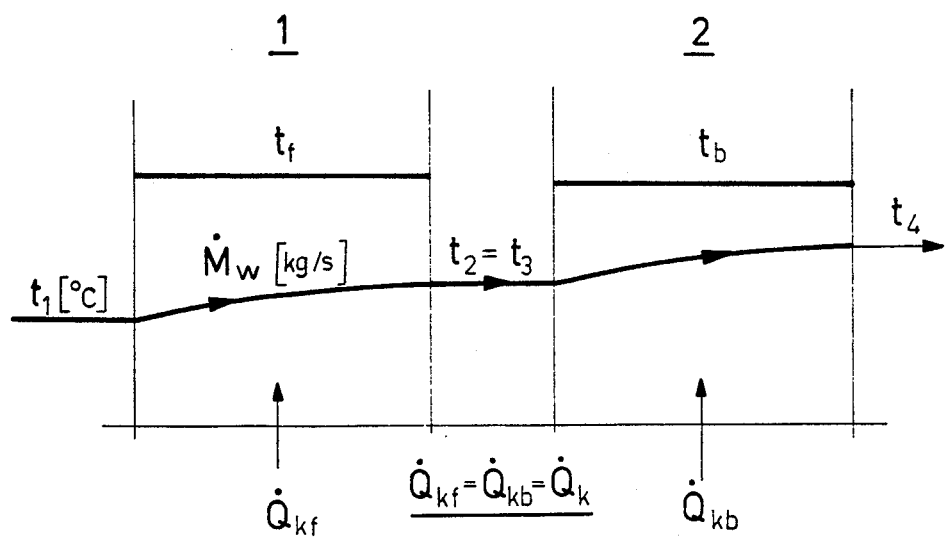
FIG. 3 is a diagram indicating the temperature progressions which are of decisive importance to the method according to the invention.

The diagram according to FIG. 3 shows the progression of the steam temperature $t_f$ and $t_b$ of the cooling water temperatures $t_1$ to $t_4$ in the condenser chambers 1 and 2 respectively as well as before, between and after the two condenser chambers, to which the same heat flows $\dot{Q}_{kf} = \dot{Q}_{kb} = \dot{Q}_k$ are supplied.

A further advantage of the method according to the invention consists in that the measurement of the steam temperature takes place directly at the tube sections 3 and 4 under quasi-static steam conditions, which is not the case in the abovementioned ASME method.

Cooling water could also flow through the two comparison tube sections 3 and 4 in the reverse sequence, but in such an arrangement the saturation steam temperatures in the two condenser chambers 1 and 2 would be more strongly differentiated, with the consequence that the equality of the coefficients of heat transfer $\alpha_f$ of the condensate films on the two comparison tube sections 3 and 4, and thus the accuracy of measurement, would no longer be guaranteed.

It is of course possible to embody the invention in other specific forms than those of the preferred embodiment described above. This may be done without departing from the essence of the invention. The preferred embodiment is merely illustrative and should not be considered restrictive in any way. The scope of the invention is embodied in the appended claims rather than in the preceding description and all variations and changes which fall within the range of the claims are intended to be embraced therein.

We claim:

1. A method of determining the thermal resistance of a deposit layer in a tubular heat exchange element of a thermodynamic apparatus caused by cooling liquid passing through said heat exchange element comprising the steps of:
   mounting a contaminated heat exchange element in a first condenser chamber, and mounting a non-contaminated heat exchange element in a second condenser chamber, said heat exchange elements being of substantially identical physical properties, except for the presence of corrosion and contamination in said contamined heat exchange element,
   feeding a cooling liquid in succession through said contaminated heat exchange element and said non contaminated heat exchange element,
   feeding a heating fluid in said first and second chambers around said contaminated and said non contaminated heat exchange elements, said cooling liquid feeding and said heating fluid feeding occurring under substantially the same thermodynamic and rheological conditions as exist in the thermodynamic apparatus,
   measuring the cooling liquid inlet and outlet temperatures of both said heat exchange elements, the mass flow of cooling liquid, the temperatures of said fluid flowing around both said heat exchange elements, and the heat flows passing to the heat exchange elements,
   determining the thermal resistances of each of said heat exchange elements,
   calculating the thermal resistance of the deposit layer from the difference of the thermal resistance of said contaminated heat exchange element and of the thermal resistance of said noncontaminated heat exchange element.

2. The method of claim 1 wherein the heat exchange element is a condenser tube contaminated in the practical operation of a power station condenser and is a single tube drawn from a bundle of condenser tubes, the method further comprising the steps of:
   subdividing said condenser tube within a water chamber of the condenser into equally long comparison tube sections the length of which is dependent on the spatial conditions in the water chambers,
   freeing a first of said comparison tube sections of said deposit layers and cleaning said first section to provide an original surface condition being used as said noncontaminated heat exchange element;
   conductively connecting a second of said comparison tube sections being used as said contaminated heat exchange element in series to said first comparison tube section,
   feeding cooling water first through the second comparison tube section and then through the first comparison tube section,
   supplying equal heat flows to the two comparison tube sections simultaneously and independently of one another, said heat flows being provided by steam,
   measuring the steady state values of the cooling water inlet and outlet temperatures at the first comparison tube section and the second comparison tube section, the mass flow of the cooling water, the steam temperatures at the two comparison tube sections, and the heat flows supplied to the comparison tube sections,
   calculating the thermal resistance of the deposit layers from one of the following calculations:

$$R_f = \pi d_a L / Q_k \cdot [(t_2 - t_1)/\ln\{(t_f - t_1)/(t_f - t_2)\} - (t_4 - t_2)/\ln\{(t_b - t_2)/(t_b - t_4)\}]$$

and, $$R_f = \pi d_a L / M_w C_{pw} \cdot [1/\ln\{(t_f - t_1)/(t_f - t)\} - 1/\ln\{(t_b - t_2)/(t_b - t_4)\}]$$

Where $R_f$ is the thermal resistance of the deposit layer, $d_a$ is the outer diameter of the comparison tube sections, L is the length of the comparison tube sections, $Q_k$ is the heat flow passing to the comparison tube sections, $t_1$ and $t_2$ are the inlet and outlet temperatures of the second comparison tube section, $t_3$ and $t_4$ are the inlet and outlet temperatures of the first comparison tube section, $t_b$ and $t_f$ are the temperatures of the fluid flowing around said first and second comparison tube sections respectively, $M_w$ is the mass flow of the cooling water, and $C_{pw}$ is the specific heat of the cooling water at a constant pressure, and where $t_2 = t_3$.

3. A device for use in determining the thermal resistance of a deposit layer in one of a bundle of condenser tubes supported in a water chamber of a power station condenser, the condenser tube having a cleaned comparison tube section and a contaminated comparison tube section having the deposit layer, each of the comparison tube sections having two ends thereon, comprising:

first and second electrically heatable condenser chambers to receive the contaminated comparison tube section and the cleaned comparison tube section respectively, said condenser chambers having steam spaces, an electrically heated degassing vessel having hot water ducts which communicate with said condenser chambers, a cooling water reservoir, a cooling water supply duct connecting said reservoir to said first condenser chamber, said supply duct having a sealing housing at a discharge end thereof to provide leak-free reception of one end of the contaminated comparison tube section, a connecting duct between said first and second condenser chambers, said connecting duct having ends extending into said chambers and sealing housings at said ends to receive in each instance a respective end of the contaminated or cleaned comparison tube section, a cooling water exhaust duct at a side of said second condenser chamber opposite said connecting duct, said exhaust duct having an end extending into said second condenser chamber and a sealing housing at said end to receive an end of said cleaned comparison tube section, means to measure a mass flow of cooling water exiting said exhaust duct, measurement chambers in said connecting duct and in at least one of said supply duct and said exhaust duct, first thermoelements positioned in said measurement chambers to measure cooling water temperatures in said ducts, second thermoelements positioned in said steam spaces for measuring the temperatures of said steam spaces of said condensers chambers, means to indicate temperature differences between two successive positions along the cooling water ducts at which said first thermoelements are positioned and between said steam spaces, a wattmeter in each of said condenser chambers to measure the heat flow passing into said condenser chambers, and regulating means to maintain said heat flows at a constant value.

4. The device of claim 3, further comprising:

water level indicators at said condenser chambers and said degassing vessel, means to evacuate said steam spaces of said condenser chambers and said degassing vessel, said means including, a vacuum pump, a first water separator upstream of said vacuum pump, a second water separator downstream of said vacuum pump, mutually communicating evacuation ducts connecting said vacuum pump with said steam spaces of said condenser chambers and said degassing vessel, first valves positioned in said evacuation ducts, compensating ducts in communication with said evacuation duct to conductively connect said steam spaces to one another, second valves in said compensating ducts, filling ducts connecting said degassing vessel with said condenser chambers, third valves positioned in said filling ducts, leakage steam ducts in communication with said evacuation ducts and conductively connecting said sealing housings in said condenser chambers to one another, said leakage steam ducts drawing-off any steam leakage currents from said sealing housings.

* * * * *